(12) United States Patent
Massaad et al.

(10) Patent No.: US 6,870,044 B2
(45) Date of Patent: Mar. 22, 2005

(54) INFLAMMATION INDUCIBLE HYBRID PROMOTERS, VECTORS COMPRISING THEM AND USES THEREOF

(75) Inventors: Charbel Massaad, Paris (FR); Francis Berenbaum, Gif sur Yvette (FR); Jean-Luc Olivier, Paris (FR); Colette Salvat, Paris (FR); Gilbert Bereziat, Palaiseau (FR)

(73) Assignee: Universite Pierre et Marie Curie, Paris (FR)

( * ) Notice: Subject to any disclaimer, the term of this patent is extended or adjusted under 35 U.S.C. 154(b) by 0 days.

(21) Appl. No.: 09/808,388

(22) Filed: Mar. 14, 2001

(65) Prior Publication Data

US 2002/0081719 A1 Jun. 27, 2002

Related U.S. Application Data

(60) Provisional application No. 60/196,959, filed on Apr. 13, 2000.

(30) Foreign Application Priority Data

Mar. 14, 2000 (FR) .............................................. 00 03262

(51) Int. Cl.[7] .................. C12N 15/00; C12N 15/09; C12N 15/86; C12P 21/06; C07H 21/04
(52) U.S. Cl. .................... 536/24.1; 536/23.1; 536/23.4; 435/69.1; 435/320.1; 435/455; 435/325
(58) Field of Search ............... 536/24.1, 23.1, 536/23.4; 435/69.1, 325, 320.1, 455

(56) References Cited

U.S. PATENT DOCUMENTS 6,413,994 B1 * 7/2002 Evans et al. ................. 514/357

FOREIGN PATENT DOCUMENTS

GB 2 269 897 2/1994

WO WO 98/21349 5/1998

OTHER PUBLICATIONS

Cyril Couturier et al, Interleukin 1B Induces Type 2–secreted Phospholipase A2 Gene in Vascular Smooth Muscle Cells by a Nuclear Factor kB and Peroxisome Proliferator–activated Receptor–mediated Process, vol. 274, No. 33, Aug. 13, pp. 23085–23093, 1999.*

C. Couturier et al., Interleukin 1Beta Induces Type II–secreted Phospholipase A2 Gene in Vascular Smooth Muscle Cells by a Nuclear Factor KappaB and Peroxisome Proliferator–activated Receptor–mediated Process, J. Biol. Chem. 274(33):23085–23093 (1999).

C. Juge–Aubry et al., DNA Binding Properties of Peroxisome Proliferator–Activated Receptor Subtypes on Various Natural Peroxisome Proliferator Response Elements., J. Biol. Chem. 272(40):25252–25259 (1997).

K. Mukhopadhyay et al., Use of a New Rat Chondrosarcoma Cell line to Delineate a 119–Base Pair Chondrocyte–speciic Enhancer Element and to Define Active Promoter Segments in the Mouse Pro–alpha1(II) Collagen Gene, J. Biol. Chem. 270(46):27711–27719 (1995).

C. Massad et al., Induction of Secreted Type IIA Phospholipase A2 Gene Transcription by Interleukin–1Beta, J. Biol. Chem. 275(30):22686–22694 (2000).

* cited by examiner

*Primary Examiner*—Gerry Leffers
(74) *Attorney, Agent, or Firm*—Young & Thompson

(57) ABSTRACT

The present invention relates to the field of the regulation of the expression of genes and is based in particular on the use of constructs which make it possible to activate the transcription of a transgene in cells, tissues or organs under inflammatory conditions. The promoters of the invention preferably comprise a) a PPAR response element and b) the whole or part of the promoter of the PLA2sIIA gene. The invention also relates to vectors, cells and compositions comprising these promoters, as well as their use for the regulation of the expression of genes in vitro, ex vivo or in vivo.

25 Claims, 5 Drawing Sheets

INFLAMMATION INDUCIBLE HYBRID PROMOTERS, VECTORS COMPRISING THEM AND USES THEREOF

The present invention relates to the field of biology. It relates in particular to the field of the regulation of the expression of genes and, more particularly, it describes the design and development of a new system for the pharmacological regulation of the expression of transgenes. The invention is based in particular on the use of constructs which make it possible to activate the transcription of the transgene in cells, tissues or organs under inflammatory conditions. The invention thus describes new compositions, constructs and methods allowing the effective regulation of the expression of a nucleic acid in vitro, ex vivo or in vivo, for example in chondrocytic cells. The applications which result from the present invention are many, in the experimental, clinical, therapeutic or diagnostic fields, for example.

Controlling the level and the duration of the expression of the transgenes is necessary for many applications. Thus, gene therapy, the production of recombinant proteins in vitro, the construction of transgenic animals, the study of the effects of a gene or of the bioavailability of a protein and the like are as many situations in which an appropriate control of genetic expression can be implemented and can bring improvements.

Gene therapy is aimed more particularly at expressing genes (or nucleic acids) which are either defective in a given individual, or which are of therapeutic interest in the context of a specific pathology. The expression of these genes requires, apart from the vectorization procedure, an induction with a promoter which binds RNA polymerase and the transcription factors required to obtain the synthesis of messenger RNA and therefore protein synthesis. Noninducible viral or eucaryotic promoters are frequently used in gene therapy to express a gene at the level of a tissue. Although it is easy to carry out, this approach does not allow the regulation of the expression of the transgene according to the environment and the external stimuli. Furthermore, the gene directed by a viral promoter will be expressed equally well in all the cells into which the vector would have penetrated, without any targeting. Finally, experimentalists have sometimes been confronted with the weakness of the expression of the viral promoter in vivo in relation to that observed in vitro.

Various artificial regulators of transcription have been designed in the prior art, which are activated by a xenobiotic molecule which binds to the promoter sequences for transcription of the transgene.

A first illustration of these regulators was constructed by fusion of the *E. coli* Lac repressor with the herpes simplex virus (HSV) VP16 transactivator domain. Two versions of these regulators exist, one capable of being activated by isopropyl β-D-thiogalactoside (IPTG) and the other inactivated by IPTG (Baim S. et al., *Proc Natl Acad Sci USA*, 88 (1991) 5072–5076; Labow M. et al., *Mol. Cell. Biol.*, 10 (1990) 3343–3356).

Another system was constructed by fusion of the *E. coli* Tet repressor with the HSV VP16 transactivator domain. Two versions of these regulators also exist, one capable of being activated by tetracycline or its derivatives and the other inactivated by these same molecules (Gossen M. and Bujard H., *Proc Natl Acad Sci USA*, 89 (1992) 5547–5551; Gossen M. et al., *Science*, 286 (1995) 1766–1769).

Another system was constructed by fusion of the DNA-binding domain of the *S. cerevisiae* GAL4 protein with the ligand-binding domain of the human progesterone receptor and the HSV VP16 transactivator domain; this version is activated by a progesterone analogue such as RU486 (Wang Y. et al., *Proc Natl Acad Sci USA*, 91 (1994) 8180–8184). A fusion of the drosophila ecdysone receptor with the HSV VP16 transactivator domain has also been described, activated by ecdysone and the analogues of this steroid hormone (No D. et al., *Proc Natl Acad Sci USA*, 93 (1996) 3346–3351). Another system takes advantage of the capacity of certain immunosuppresive molecules (cyclosporin A, rapamycin and its derivatives) to promote the combination of certain cellular proteins. A transcriptional regulator then consists of two protein subunits; the first may be formed by the fusion of a chimeric DNA-binding domain and of three copies of the human FKBP protein and the second by the fusion of the rapamycin-binding domain of the human FRAP protein and of the transactivator domain of the human NFκB p65 subunit. This transcriptional regulator is activated by rapamycin which allows the dimerization of the two subunits (Rivera V. et al., *Nat. Med.*, 2 (1996) 1028–1032).

Although these systems make it possible to obtain satisfactory levels of regulation in some tissues, they exhibit, nevertheless, certain disadvantages which limit their conditions of use. Thus, these transcriptional regulators are xenogenic proteins in humans. They indeed consist of protein fragments obtained from bacteria, viruses, yeasts or insects or, when the protein domains are of human origin, their joining creates sequences which are foreign to humans. These protein domains may therefore induce a cytotoxic immune reaction, causing the destruction of the cells which express the gene of interest under the control of the xenogenic transcriptional regulator, and thus the termination of the expression of the transgene. This situation may necessitate the use of repeated administrations of the therapeutic gene, which constitutes a major disadvantage, in particular when this involves a traumatic surgical act, and which is not always effective, in particular when the vector of the therapeutic gene is a virus whose first injection causes an immune reaction. In addition, the levels of expression observed with the prior art systems of regulation are not always satisfactory.

The present invention now describes a new improved system for the controlled expression of nucleic acids in cells. This invention provides a hybrid promoter which is inducible by the principal mediators of inflammation and by exogenous compounds. This promoter preferably leads to the expression of a gene at the level of the tissue which is the seat of an inflammation, in response to the mediators synthesized during the inflammatory process. The principal benefit of this promoter lies in the possibility of an expression of the gene-medicament which can be modulated according to the intensity of the inflammation. Furthermore, the expression of the gene maybe increased if NSAIDs are being taken. This is therefore an approach which is transposable to many inflammatory situations for which a gene therapy is envisaged.

The present invention consists more particularly in the construction of a hybrid promoter comprising a module for responding to the PPARs and a module for responding to the cytokines produced during inflammation. This second module comprises more particularly sequences derived from the promoter of the gene for type IIA-1 nonpancreatic secreted phospholipase A2 (PLA2s), which is expressed in some human cells, in particular the chondrocytes, under inflammatory conditions. The combination of these two modules makes it possible to generate a promoter allowing a specific expression of genes under inflammatory conditions, which expression may be increased by exogenous anti-inflammatory medicaments or mediators. As will be illustrated in the examples, this hybrid promoter preferably possesses a low basal activity, but a very high activity under induction conditions. This type of promoter is therefore particularly suitable for the expression of products having an anti-inflammatory activity, as will be explained in detail in the remainder of the text. The promoters of the invention are most particularly advantageous for the expression of genes in articular tissues, in particular the chondrocytes, in different pathological situations in which an inflammatory component is present, and in particular osteoarthritis.

Osteoarthritis is a disease of aging which is accompanied by articular destruction which causes a variable degree of invalidity (Chevalier X, 1998). The treatment of this pathology is currently considered as a priority in terms of public health because of its frequency and the handicap which it causes. From a physiopathological point of view, even though the mechanisms of initiation still remain poorly understood, the tissue target responsible for the articular destruction is the cartilage, a tissue composed of an extracellular matrix rich in type II collagen and in proteoglycans and articular chondrocytes, sole cartilage cell type, which are responsible for the matrix synthesis. The chondrocytes also secrete growth factors and natural protease inhibitors (anabolic activity) as well as proteases (catabolic activity). Physiologically, there is an equilibrium between these activities (cartilaginous homeostasis). During osteoarthritis, there is a disequilibrium at the expense of the anabolic activity because of the stimulation of the synthesis of proteases (essentially metalloproteases) and an inhibition of the synthesis of inhibitors of metalloproteases (TIMP or tissue inhibitor of metalloproteases) (Lefebvre V et al., 1997; Dean J et al., 1990; Hornebeck W, 1990). These modifications in synthesis are due to the presence of pro-inflammatory mediators produced by the chondrocytes and found in large quantities in the synovial fluids of patients suffering from osteoarthritis or from rheumatoid arthritis, cytokines (IL-1, TNF) and lipid mediators, in particular prostaglandin E2. This prostaglandin stimulates the synthesis of collagen in low concentration like the growth factor but inhibits in high concentration (Di Battista J A et al., 1996).

The present invention now provides hybrid transcriptional promoters which are particularly suitable for the expression of therapeutic genes in articular pathologies such as osteoarthritis. In addition, the invention also describes constructs allowing screening of the transfer and/or of the expression of a gene of interest into the chondrocytes, further improving the advantageous properties of the constructs for this type of applications.

A first subject of the invention consists more particularly in a hybrid promoter comprising:
a) a PPAR response element and
b) the whole or part of the promoter of the PLA2s IIA gene.

The present invention consists in particular in the demonstration that this type of construct produces a synergistic effect on the expression activity, without impairing the regulated and specific (or preferential) nature of inflammatory situations. The invention also describes vectors, plasmids and compositions comprising these promoters, as well as their uses for the expression of genes in vitro, ex vivo or in vivo.

The first element of the hybrid promoters of the invention therefore comprises a PPAR response element. PPARs (Peroxisome Proliferator-Activated Receptors) belong to the superfamily of nuclear receptors comprising the receptors for steroid hormones, the receptors for thyroid hormones, for renitoic acid and for vitamin D (Schoonjans K et al., 1996). PPARs exist in three isoforms: PPARα, PPARβ and PPARγ. The PPARs bind to specific sequences at the level of the promoters of target genes (PPRE sequences), and induce the expression of these genes.

A PPAR response element (PPRE, "Peroxysome Proliferator Response Element") is therefore a nucleic acid region capable of binding a PPAR, it being possible for the binding of the PPAR to then mediate a signal around neighboring nucleic regions, in particular the regions derived from PLA2s according to the invention. A PPAR response element according to the invention is more particularly a nucleic acid region capable of binding a PPAR, whether it is a PPARα, β or γ. It is still more preferably a nucleic acid capable of binding a PPARα or a PPARγ. For carrying out the invention, the PPAR response element comprises more particularly one or more PPAR-binding sites. Such binding sites have been described in the prior art, such as, for example, in different human promoters (consensus site DR1, gene for apolipoprotein AII, for example). Such sites may also be artificially constructed, and tested for their PPRE properties, as is described below.

In a specific embodiment of the invention, the PPAR response element comprises one or more sites having the sequence CAAAACTAGGTCAAAGGTCA (SEQ ID NO:1) or functional variants of this sequence. The sequence SEQ ID NO:1 corresponds to the consensus region DR1.

The term functional variant designates any modified sequence conserving the properties of PPRE as mentioned above, that is to say in particular the capacity to bind a PPAR. The modifications may comprise one or more additions, mutations, deletions and/or substitutions of nucleotides in the sequence considered. These modifications may be introduced by conventional molecular biology methods, such as in particular site-directed mutagenesis or, more practically, by artificial synthesis of the sequence in a synthesizer. Generally, the variants conserve at least 50% of the residues of the initial sequence indicated. More preferably, the variants possess modifications affecting less than 8 nucleotides in the sequence considered. The variants thus obtained are then tested for their PPRE activity. This property may be checked in various ways, and in particular:

(i) by bringing the test sequence into contact with a PPAR (for example in an acellular test), and detecting the formation of a complex (for example by gel migration retardation);

(ii) by inserting the test sequence into an expression cassette comprising a minimal promoter and a reporter gene, introducing the cassette into a cell, and detecting (where appropriate assaying) the expression of the reporter gene in the presence and in the absence of a PPAR and of a ligand for a PPAR;

(iii) by any other technique known to a person skilled in the art, making it possible to detect the interaction between a nucleic acid and a protein, for example.

A variant is considered to be functional for the purpose of the present invention when the activity measured, for example in (ii) above, is preferably at least equal to 50% of that measured with a site having the sequence SEQ ID NO:1, more preferably at least equal to 75%. Functional variants of PPAR-binding sites for the purpose of the invention are described, for example, in Juge-Aubry et al. (J. Biol. Chem. 272 (1997) 25252) and in Nakshatri et al. (NAR 26 (1998) 2491), which are incorporated into the present application by way of reference.

Specific examples of PPAR response elements according to the invention are represented by the elements (DR1)2 17

(SEQ ID NO:2), (DR1)2 21 (SEQ ID NO:3) and (DR1)2 31 (SEQ ID NO:4) as described in the examples, or functional variants thereof.

Another variant is a fragment having the sequence SEQ ID NO:1, comprising residues 8–20 thereof.

The sequences SEQ ID NO:1–4 according to the invention represent PPREs essentially corresponding to PPARα and γ. As illustrated in the examples, these sequences possess high inducibility by the PPARs, linked in particular to the particular arrangement of the binding sites. In this regard, a particular subject of the invention also consists in a nucleic acid comprising a sequence chosen from SEQ ID NOS:2–4.

According to another particular embodiment, the PPAR response element comprises one or more J sites of the human apoAII promoter (nucleotides −734 to −716) or functional variants of this sequence, which corresponds to activation by the PPARβs.

As indicated above, in the compositions according to the invention, the PPAR response element may comprise several sites for binding to a PPAR. This may be a repetition of the same site, or combinations of different sites, the repetition of identical sites being preferred. More particularly, the response element comprises up to 30 binding sites, preferably from 3 to 20, more preferably from 1 to 5. A preferred embodiment of the invention is a construct comprising 2 DR1 binding sites, the results presented in the examples showing the advantageous properties of such constructs in terms of induction and of levels of expression, in particular in the chondrocyte cells (SEQ ID NO: 2–4).

For the preparation of a hybrid promoter according to the invention, the PPAR response element (a) is combined with the whole or part of the PLA2s IIA-1 promoter (element b)).

The nonpancreatic secreted phospholipase A2 is a protein activated by interleukin-1 beta, and leads to the production of inflammation mediators, in particular lipid mediators (prostaglandin E2). In particular, prostaglandin PEG2 is derived from the activation, by interleukin-1 (IL-1), of nonpancreatic secreted phospholipase $A_2$ ($PLA_2s$) (Nevalainen T J et al., 1993; Hulkower K J, 1997) and releases arachidonic acid from phospholipids and of inducible cyclooxygenase (COX-2) (Amin A R, 1997; Geng Y et al., 1995; Knott et al., 1994), the latter converts the arachidonic acid to PGH2. PGH2 is then converted to PGE2 by PGE synthase. Two types of phospholipase $A_2$ have been identified in human cells, in particular the chondrocytes. The nonpancreatic secreted phospholipase $A_2$ ($PLA_2s$) is a 14 kDa protein which is abundantly synthesized and secreted in inflammatory synovial fluids (Seilhamer J J et al., 1989). Cytosolic phospholipase $A_2$ ($PLA_2c$) is a cytosolic protein of 85 Kda whose activation occurs via its phosphorylation by the MAP kinases and its translocation to the membrane (Clark J D et al., 1991). IL-1 induces the expression of the COX-2 and $PLA_2s$ genes without affecting that of the $PLA_2c$ gene in the chondrocytes (Berenbaum F et al., 1994; Jacques C et al., 1997). The levels of secreted $PLA_2$ in the joint and in the serum are correlated with the level of inflammation, in particular the level of osteoarthritis in the case of the chondrocytes (Pruzanski W et al., 1994; Lin M et al., 1996). The cooperation between PLA2s and COX-2 results in a sustained production (>48 hours) of prostaglandin PGE2 under IL-1β stimulation (Bingham C O et al., 1996; Kuwata H et al., 1998) whereas PLA2c and the constitutive cyclooxygenase COX-1 would be responsible for an early response. In our previous studies, a correlation had been shown between the synthesis of PGE2 and the level of activity of $PLA_2s$ linked to the chondrocytic membranes (Jacques C et al., 1997).

The present invention now proposes using the whole or part of the promoter of the PLA2s gene for regulating the expression of nucleic acids of interest, in therapeutic applications in particular. The invention proposes in particular using the whole or functional parts of the PLA2s IIA promoter for the construction of a regulated hybrid promoter active in cells exhibiting an inflammatory situation. In this regard, the applicants have shown that a fragment of 247 base pairs upstream of the first exon of the human gene for PLA2s IIA (SEQ ID NO:5) was responsible for a stimulation 6 to 8 times the activity of the CAT reporter gene by IL1β in rabbit chondrocytes in primary culture. Three regulatory regions were characterized in this promoter: the proximal region (−85/−114) ensures a basal transcriptional activity and binds the factor Sp1; the distal region (−247/−210) binds members of the NF1 family and the receptor for the glucocorticoids, which stabilize the binding of the C/EBP factors between positions −198/−190 relative to the site of initiation of transcription. The family of C/EBP factors comprises three principal activating members C/EBPα, C/EBPβ and C/EBPδ. The factors C/EBPβ and C/EBPδ are activated at the transcriptional and post-transcriptional level by the pro-inflammatory cytokines. They are expressed in the chondrocytes whereas C/EBPα is not. C/EBPβ and C/EBPδ are responsible for the activation of the transcription of the gene for sPLA2-IIA by ILL1β. The applicants have now shown that they are also critically involved in the induction of the transcription of the gene for COX-2 by IL-1β in human and rabbit chondrocytes.

In a specific embodiment, element b) of the hybrid promoters of the invention comprises the whole or part of the sequence SEQ ID NO:5 or of a functional derivative thereof. The sequence SEQ ID NO:5 corresponds to nucleotides −247 to +20 of the human gene for PLA2s IIA (residues 5 to 271).

The term <<part>> designates more particularly any fragment of the sequence considered which conserves biological functionality. This is more particularly a part ensuring a basal transcriptional activity for the hybrid promoter (TATA box, for example) and a character regulatable by the inflammation mediators, in particular by interleukin-1β.

In this regard, a preferred variant of the invention relates to a hybrid promoter comprising at least part of the PLA2s IIA promoter conferring induction by interleukin-1β.

More particularly, element (b) of a hybrid promoter according to the invention may comprise the following sequences:

at least residues 51 to 61 of SEQ ID NO:5 (corresponding approximately to residues −200/−191 of the human PLA2s IIA gene), involved in the regulation by IL1, and/or, at least residues 23 to 32 of SEQ ID NO:5 (corresponding approximately to residues −229/−220 of the human PLA2s IIA gene), representing a half site NF1 and a half site GRE (these sequences are involved in the regulation by certain compounds such as dexamethasone), and/or at least residues 148 to 155 of SEQ ID NO:5 (corresponding approximately to residues −104/−97 of the human PLA2s IIA gene), involved in the binding of Sp1, and/or at least residues 5 to 170 of SEQ ID NO:5 (corresponding approximately to residues −247/−85 of the human PLA2s IIA gene), or alternatively at least residues 51 to 170 of SEQ ID NO:5 (corresponding approximately to residues −200/−85 of the human PLA2s IIA gene).

A specific example of a hybrid promoter comprises a PPAR response element (DR1)2 21 linked to fragment −247/+20 of the PLA2s IIA gene. Such a promoter comprises the sequence SEQ ID NO:6, which is also a specific subject of the present invention. In this sequence, the PPRE element essentially corresponds to residues 13–53 and the PLA2s element to residues 62–332. Residues 1–12 and 54–61 correspond to neutral regions from the functional point of view, resulting from clone steps and making it possible to modify the structure of the promoter (cloning sites).

Of course, sequence variations may occur in the regions considered, without substantially affecting the transcriptional activity of the hybrid promoter of the invention (mutations, deletions, substitutions, insertions and the like), in particular on one to five bases. It is understood that such variants represent specific embodiments of the present invention.

The PPAR response element (PPRE) and the region derived from PLA2s IIA are functionally arranged in the hybrid promoter of the invention, that is to say such that the hybrid promoter exerts a transcriptional activity in the presence of inflammation mediators, preferably regulated by the PPRE element.

Preferably, element a) is positioned upstream (in 5') of element (b) in the hybrid promoter (cf. FIG. 1). This configuration indeed makes it possible to ensure a high and regulated level of expression in the cells, in the presence of inflammation mediators (LTB4) and/or of PPAR activators.

The different functional domains above can be linked directly to each other, or separated by or combined with nucleotides which do not significantly affect the regulated nature of the promoter. Such nucleotides may be residues which are neutral from the functional point of view, resulting for example from cloning steps (PCR ends, restriction sites and the like). These nucleotides may also possess biological properties, making it possible to confer improved characteristics or performance on the system of the invention (enhancer of housekeeping genes, tissue-specific enhancer, silencer, intron, splicing site and the like). In this regard, in a particular embodiment of the invention, the hybrid promoter comprises, in addition, an element c) conferring tissue specificity. This element c) may be located between elements a) and b), or downstream (3') of element b). The term <<tissue specificity>> designates a preferential or predominant expression in a given (type) of cells, without however completely excluding a residual or lower expression in other cells.

A specific embodiment of the invention consists more specifically in a hybrid transcriptional promoter comprising, in the 5'→3' orientation:
a) a PPARα and/or γ response element preferably comprising the whole or part of a sequence SEQ ID NO:1 to 4,
b) the whole or part of the sequence SEQ ID NO:5, and
c) where appropriate, an element conferring tissue specificity.

In a specific application, element c) confers specificity of expression for the chondrocytic cells, and in particular it comprises the whole or part of the sequence SEQ ID NO:7 or of a variant thereof. This type of promoter is particularly suitable for the regulated and selective expression of nucleic acids in the chondrocytes, in particular in an inflammatory situation (osteoarthritis).

The cartilaginous matrix consists of a large number of collagenous and noncollagenous proteins. Some genes encoding proteins of this matrix are specifically expressed by the chondrocyte like the genes for type II collagen, agrecan, matrilin-1 (or cartilage matrix protein) and chondroadherin. The latter two proteins interact specifically with integrins synthesized by the chondrocytes and are responsible for anchoring of the cell to the other components of the matrix (Makihira S et al., 1999; Camper L et al., 1997). The expression of the genes for type II collagen and agrecan have been widely cited in the literature as positive markers of chondrocytic differentiation whereas the synthesis of type I collagen marks a phenomenon of dedifferentiation (Benya P et al., 1986). The group of Pr de Crombrugghe has identified a sequence of 18 base pairs which is necessary and sufficient to direct the expression of type 11 collagen in the chondrocytes. This sequence binds a nuclear factor (SOX9) which is moreover thought to be involved in chondrocytic differentiation (Mukhopadhyay K et al., 1995; Zhou G et al., 1995). This factor is colocalized with the expression of type II Collagen in the primary chondrocytes. It binds to the sequence CATTCAT at the level of the promoter of the type II collagen gene and activates its transcription.

For the gene of interest to no longer be expressed only in an inducible manner but also specifically in the chondrocyte, elements of the promoter of type II collagen which are capable of binding the SOX factors (SOX9, SOX6 and L-SOX5) (Mukhopadhyay K et al., 1995; Zhou G et al., 1995; Lefebvre V et al., 1997) may be integrated. A nucleotide sequence described by Zhou et al. (1995) and Lefebvre V et al. (1997) formed of a duplicate of 231 bp of the first intron of type II collagen may be used. This construct proved to be the most effective in the system. It can be inserted downstream of the hybrid construct (DR1)2 21 -promoter of sPLA2IIA, by including splice donor (SD) and acceptor (SA) sites on either side, this being with the aim of constituting a first synthetic intron following the first exon of 20 untranslated base pairs of the gene for sPLA2-IIA as schematically represented in FIG. 7A. The insertion of a first intron generally facilitates the expression of the transgene situated downstream. This insertion would make it possible, on the one hand, to restrict and, on the other hand, to enhance the expression of the transgene in the chondrocytes by virtue of the presence of the site for the Sox9 factor. In another construct, the sequence containing the sites for binding the Sox factors as a promoter may be inserted before the sites for binding the PPARs as schematically represented in FIG. 7B.

Another subject of the invention relates to any nucleic acid comprising a hybrid promoter as defined above and a gene of interest. The gene of interest may be any nucleic acid (cDNA, gDNA, synthetic or semisynthetic DNA, RNA, and the like), of diverse origin (of animal, human, plant, bacterial, viral or artificial origin, and the like), encoding a product of interest (RNA, polypeptide or peptide). It is advantageously a nucleic acid encoding an anti-inflammatory product, that is to say a product capable of restoring or of reducing the inflammatory phenomena in a cell, tissue or organ. Among the anti-inflammatory products, there may be mentioned in particular TIMP or other cytokines or enzymes capable of reducing the inflammatory phenomenon. The product of interest may be, more generally, any enzyme, hormone, growth factor, antibody, immunogenic peptide, lipoprotein, toxin, antibody or antibody fragment, antisense, transcription factor and the like, of therapeutic or vaccinal interest.

The gene of interest is generally placed downstream (3') of the hybrid promoter, under the transcriptional control of the latter. Thus, a preferred nucleic acid for the purposes of the invention comprises, in the 5'→3' orientation:
a) a PPARα and/or γ response element preferably comprising the whole or part of a sequence SEQ ID NO:1 to 4, b) the whole or part of the sequence SEQ ID NO:5,
c) where appropriate, an element conferring tissue specificity, and
d) a gene encoding a product of interest, in particular of therapeutic or vaccinal interest.

Another subject of the invention consists in a vector comprising a hybrid promoter or a nucleic acid as defined above. The vector may be of varied, in particular plasmid, episomal, chromosomal, viral or phage, nature and/or origin, and the like. Preferably, the vector is a plasmid or a recombinant virus, more preferably a plasmid.

As an example of a viral vector, there may be mentioned in particular a recombinant adenovirus, a recombinant retrovirus, an AAV, a herpesvirus, a vaccinia virus and the like, whose preparation may be carried out according to methods known to persons skilled in the art.

As regards the plasmids, there may be mentioned any replicative or integrative plasmid which is compatible with use in mammalian, in particular human, cells.

Another subject of the invention consists in a composition comprising a nucleic acid or a vector as defined above. The composition may contain, moreover, any vehicle acceptable for administration in vivo or ex vivo of constructs (in particular any pharmaceutically acceptable vehicle), and/or for a stable storage thereof. As vehicle, there may be mentioned in particular isotonic, buffered, saline solutions optionally comprising additives such as high-molecular weight proteins or polymers. Moreover, the compositions of the invention may comprise agents which facilitate the penetration of the genetic constructs of the invention into cells. There may be mentioned in particular lipids, polymers, peptides and the like, which make it possible to improve cellular transfection.

To this effect, a particular composition according to the invention comprises one or more polycationic lipids, optionally coupled to polycationic polymers. This type of formulation is particularly suitable for the transfer of genes into the chondrocytes, which are surrounded by a matrix rich in negatively charged proteoglycans. Polycationic lipids can therefore become easily integrated into this matrix. The addition of polycationic polymers such as PEI (polyethylenimine) comprising incompletely protonable amines at the physiological pH makes it possible to increase the efficiency of transfection of the chondrocytes. These amines function as a sponge for protons with endosomolytic properties. The combination consisting of the cationic lipids, the PEI and the plasmid carrying the transgene constitutes a particular composition which is preferred in the context of the present invention.

Moreover, the compositions of the invention may also comprise one or more targeting elements which make it possible to ensure a preferential transfection toward desired cell types. In this context, the targeting elements may consist of ligands for specific receptors, receptors for ligands, antibodies or antibody fragments, and the like.

For targeting toward chondrocytic cells, a preferred composition for the purposes of the invention comprises, in addition, one or more molecules which possess affinity for the chondrocytic membrane. Among these proteins, there may be mentioned in particular the Chondroadherin protein, which interacts with a good affinity with integrin alpha2 beta1 of the chondrocytes (Camper L et al., 1997). It is a small protein of 36 kDa, rich in leucine. This protein may be produced (for example in a recombinant baculovirus), purified and incorporated into a composition (in particular a liposome) of the invention. The hydrophobicity of the protein can, moreover, be increased by addition of a farnesylation sequence at the C-terminal like the Q-Ras4B end (Leevers S J et al., 1994; Stokoe D et al., 1994; Zlatkine et al., 1997).

It is understood that any other targeting element may be envisaged, depending on the desired applications.

Moreover, another subject of the invention further consists in a composition comprising (i) a nucleic acid or a vector as defined above and (ii) a PPAR activator, for use simultaneously, separately or spaced out over time.

As indicated above, the hybrid promoters comprise a PPAR response element. This PPAR may be released (or induced) into the cells, for example in an inflammatory situation, or also in the presence of exogenous activators (i.e. added or administered). In this context, the expression << for use simultaneously, separately or spaced out over time >> indicates that the vector and the activator may be prepared separately, packaged separately and used sequentially, to allow control of the expression of the nucleic acid of interest. Typically, the vector and the activator are packaged separately and used spaced out over time, the combination of these different elements in a cell, tissue or organ, and the like, leading to the desired effect of regulating or enhancing expression.

Depending on the hybrid promoter or the desired applications, various types of ligands, natural or synthetic, may be used. Thus, this may be preferably a PPARγ activator and/or a PPARβ activator and/or a PPARα activator.

The PPARγ-activating ligands may be chosen from natural or synthetic ligands. As natural ligands, there may be mentioned fatty acids and eicosanoids (for example linoleic acid, linolenic acid, 9-HODE, 5-HODE) and, as synthetic ligands, there may be mentioned thiazolidinediones, such as in particular rosiglitazone (BRL49653), pioglitazone or troglitazone (see for example Krey G. et al., *Mol. Endocrinol.*, 11 (1997) 779–791 or Kliewer S. and Willson T., *Curr. Opin. in Gen. Dev.* 8 (1998) 576–581), the compound RG12525 or 15 dioxy-Δ12–14 PGJ2.

The PPARα-activating ligands are, for example, the fibrates such as fibric acid and its analogs. As analogs of fibric acid, there may be mentioned in particular gemfibrozyl (Atherosclerosis 114(1) (1995) 61), bezafibrate (Hepatology 21 (1995) 1025), ciprofibrate (BCE&M 9(4) (1995) 825), clofibrate (Drug Safety 11 (1994) 301), fenofibrate (Fenofibrate Monograph, Oxford Clinical Communications, 1995), clinofibrate (Kidney International. 44(6) (1993) 1352), pirinixic acid (Wy-14,643), 5,8,11,14-eicosatetranoic acid (ETYA), or the nonsteroidal anti-inflammatory agents (NSAID) such as ibuprofen and indomethacin. These different compounds are compatible with a biological and/or pharmacological use in vitro or in vivo.

Moreover, the compositions according to the invention may comprise several PPAR activators in combination, and in particular a fibrate or a fibrate analog combined with a retinoid.

These different ligands may be used at conventional doses which are described in the prior art and are illustrated in the examples.

The compositions according to the invention may be formulated in any suitable type of material, such as a tube, ampoule, bag, vial, syringe and the like, and stored in the cold (or frozen) or in freeze-dried form.

The invention may be used for expressing a gene in various types of cell, tissue or organ, in vitro, ex vivo or in vivo. In particular, this may be a mammalian, preferably human, cell, tissue or organ, in particular in an inflammatory state. By way of illustration, there may be mentioned chondrocytic cells (or cells of the bone matrix) muscle cells (or a muscle), hepatic cells (or the liver), cardiac cells (or the heart, the arterial or vascular wall), nerve cells (or the brain, the marrow and the like) or tumor cells (or a tumor).

Preferably, the constructs, compositions and method of the invention are used for the regulated expression of a nucleic acid in a chondrocytic cell in vitro, ex vivo or in vivo. The results presented in the examples illustrate more particularly the advantages of the invention in vivo or in vitro in this type of cells.

The invention also relates to the use of a vector as defined above for the preparation of a composition intended for inducing the expression of a gene in a tissue in an inflammatory situation. It also relates to a method for the expression in a gene in a tissue in an inflammatory situation, comprising the administration of a vector or of a composition above to a subject.

Advantageously, it involves a use or a method for the expression of a gene in a chondrocyte.

The invention also relates to the use of the above nucleic acids, vectors or compositions for the treatment of osteoarthritis.

For a use in vitro or ex vivo, the cells may be brought into contact with the compositions or vectors of the invention according to various protocols. Thus, the cells in culture may be incubated directly with the vectors or compositions of the invention, for example with a vector comprising the hybrid promoter and a gene of interest, where appropriate in the presence of the activator. Alternatively, the cells may be incubated in a first stage with the vector or nucleic acid and then, in a second stage (after culture and optionally selection of the modified cells), the activator may be added. These experiments may be carried out in any appropriate medium and device, preferably in a plate, dish, flask, under sterile conditions. The quantities of cells, vector and ligand can be easily adapted by persons skilled in the art, on the basis of the information provided in the examples and of their general knowledge.

For a use in vivo, the cells (or organs, tissue and the like) are brought into contact by administration of the nucleic acids, vectors or compositions in vivo, simultaneously, separately or spaced out over time. To this effect, the vectors, compositions or nucleic acids are generally administered by the parenteral, in particular intramuscular, intravenous, subcutaneous, intradermal, intratumoral, intrabone, intraarticular or stereotaxic route. The choice of the mode of administration may be guided by the application envisaged, the tissue targeted and/or the type of product of interest encoded by the transgene. For this administration, the compositions of the invention may comprise any agent promoting cellular transfection (cationic polymer, lipid and the like).

The activator may be administered before, simultaneously or after the vectors or nucleic acids. In this regard, the administration of the ligand may be carried out by the oral, anal, intravenous, intraperitoneal, intraocular or intramuscular route, for example.

The doses used may be adapted by persons skilled in the art, on the basis of the in vivo data published in the literature. Thus for example, for a form not soluble in water, typical doses of ligand such as BRL 49653 are between 5 and 50 mg/kg, for example 30 mg/kg, which make it possible to obtain a plasma concentration close to about 15 µg/ml at least. For a water-soluble form of ligand, whose bioavailability is greater (for example a maleate salt of BRL49653), the typical doses are lower, generally less than 5 mg/kg, for example from 0.01 to 1 mg/kg. These doses can be quite obviously adapted by persons skilled in the art as a function of the constructs used, the ligands used, and the desired applications and effects. Moreover, repeated administrations of ligand may be carried out.

In general, the doses of vector used may vary between 0.01 and 1000 µg, or more, depending on the desired applications.

In a typical experiment, a vector according to the invention is administered by the local route (directly into the affected tissue, for example the seat of inflammation, in particular by the intraarticular route) in the presence of a transfecting agent. Under the effect of the mediators released by the cells (PG2, IL1, LTB4, and the like), an expression of the gene of interest is observed which may be stimulated or enhanced by administration of one or more PPAR ligands, as defined above, or in the presence of endogenous PPARs.

Thus, the release of arachidonic acid and of other fatty acids by phospholipases $A_2$ results in the synthesis of other icosanoids and lipid mediators. These mediators activate the transcription factors PPARs (Peroxisome Proliferator-Activated Receptors). These factors are also activated by certain medicaments such as hypolipemic fibrates, the thiazolidinediones used in diabetes and the nonsteroidal anti-inflammatory drugs (NSAIDs) (Lehmann J M et al., 1997). The chondrocytes express the PPARα and PPARγ factors (Bordji et al., J. Biol. Chem., in press). The icosanoids (derivatives of arachidonic acid) such as the prostaglandins (PGE2, PGJ2) induce PPARγ (Kliewer S A et al., 1995; Krey G et al., 1997); in particular, prostaglandin 15 dioxy Δ12–14 PGJ2 is the most potent activator of PPARg. The leukotriene LTB4 and the fibrates activate PPARα (Devchand RP et al., 1996) and the long fatty acids activate the two isoforms PPARα and γ.

The results presented in the examples illustrate the synergistic properties of the hybrid promoters, in the presence of two activating signals.

The invention also relates to any cell modified by bringing into contact with a composition or a vector as defined above, especially any mammalian, in particular human, cell, more specifically chondrocytes.

The invention also relates to various fragments of the PLA2s promoter as described above, which can be used for example to confer a regulatable character to promoters.

The present invention will be described in greater detail with the aid of the following examples which should be considered as illustrative and nonlimiting.

MATERIALS AND METHODS

Figure 1:
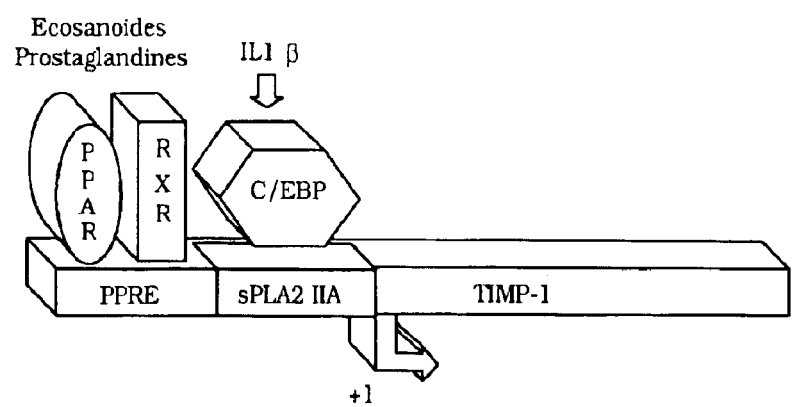
FIG. 1: Schematic representation of a hybrid promoter of the invention controlling the expression of TIMP1.

1-Cell Cultures and Transfections.

The hind and forelegs of 3-week-old prepubescent rabbits (Fauve de Bourgogne) were dissected and chopped up under sterile conditions. The cartilage is removed with a scalpel and then the chondrocytes are dissociated by means of proteolytic enzymes: hyaluronidase 0.05% for 15 minutes, trypsine 0.25% for 30 minutes and collagenase 0.2% for 90 minutes. Finally, the HAM's F12 medium is added for 60 minutes. The suspension of chondrocytes is cultured in dishes 6 cm in diameter (150,000 cells per dish) in the presence of HAM's F12 medium containing 10% fetal calf serum. Under these conditions, the chondrocytes have a differentiated phenotype as the production of type II collagen demonstrates.

When these cells reach preconfluence (6 to 7 days), they are transfected with the various constructs using the calcium phosphate method.

2-Measurement of the CAT and β-galactosidase Activities.

The CAT activity is measured according to the double liquid phase technique according to Desbois et al. (1992). The β-galactosidase activity is measured with the aim of normalizing the variations in the transfection efficiency.

3-Preparation of the Nuclear Proteins and Retardation Experiments in Electrophoresis.

The Cos-1 cells (transformed monkey kidney fibroblasts) are transfected according to the abovementioned calcium phosphate technique using 20 μg of vectors for expression of PPARγ, PPARα or RXR. Non-transfected Cos-1 cells will serve as control. 48 hours after the transfection, the cells are incubated with a buffer containing KCl (0.45 M), Tris-HCl (20 mM, pH=7.5) and 10% glycerol. They are detached by scraping and then disrupted by cooling to −80° C. and thawing at 37° C. These cells are then centrifuged at 15,000 rpm, for 10 minutes at 4° C. The supernatant is then frozen at −80° C. and used for the gel retardation experiments.

4-Gel Retardation Experiments.

The sequences DR1, (DR1)2 17, (DR1)2 21, and (DR1)2 31 are radiolabeled by means of the Klenow fragment of DNA polymerase using [α-$^{32}$P]dCTP. One hundred thousand cpm (0.4 ng) of the radiolabeled probes are incubated, for 30 minutes at 4° C., with increasing quantities of Cos-1 extracts enriched with PPAR and RXR (as indicated in the legend to the figures) and with a specific binding buffer (KCl 100 mM, Hepes 40 mM, pH 7.5, NP40 0.1%, ZnCl$_2$ 0.5 mM, PEG 8%). The mixture is then deposited on an acrylamide/bisacrylamide gel (5%, TBE 0.25×) and run for 2 hours 30 min at 200 volts. The gel is then dried and autoradiographed.

5-Molecular Biology

The methods commercially used in molecular biology such as preparative extractions of plasmid DNA, centrifugation of plasmid DNA in a cesium chloride gradient, electrophoresis on agarose gels, purification of DNA fragments by electroelution, precipitation of plasmid DNA in saline medium with ethanol or isopropanol, transformation in *Escherichia coli* are well known to persons skilled in the art and are widely described in the literature (Sambrook et al., "Molecular Cloning, a Laboratory Manual", Cold Spring Harbor Laboratory, Cold Spring Harbor, N.Y., 1989).

The plasmids are of commercial origin.

The enzymatic amplification of the DNA fragments by the PCR technique (Polymerase Chain Reaction) may be carried out using a DNA thermal cycler™ (Perkin Elmer Cetus) according to the manufacturer's recommendations.

The electroporation of plasmid DNA into *Escherichia coli* cells may be carried out with the aid of an electroporator (Bio-Rad) according to the manufacturer's recommendations.

The verification of the nucleotide sequences may be carried out by the method developed by Sanger et al. (*Proc. Natl. Acad. Sci. USA*, 74 (1977) 5463–5467) using the kit distributed by Applied Biosystems according to the manufacturer's recommendations.

EXAMPLES

In the experimental section which follows, there have been described the construction and use of several hybrid promoters of the invention, comprising an element inducible in particular by IL1b and an element inducible by icosanoids, fatty acids and nonsteroidal anti-inflammatory agents (NSAID).

The first module comprises in particular the region [−247; +20] (relative to the site of initiation of transcription of sPLA2). This region contains the TATA box and the proximal element (−114/−85) which is essential for the transcriptional activity and which binds the ubiquitaire factor Sp1. It also comprises the site C/EBP (−198/−190) essential for stimulation by IL-1β and the element [−247/−210] which enhances the activity of the C/EBP factors. Furthermore, this module contains a glucocorticoid response element capable of relaying induction by these hormones.

The addition of the second module is intended to enhance the induction during the inflammatory process by the mediators derived from the fatty acids produced by the inflammation (prostaglandins, leukotrienes) or by exogenous compounds (fibrate, nonsteroidal anti-inflammatory drugs-NSAID). This module comprises a PPARs response element (PPRE) situated upstream of the first module.

Example 1

Construction of PPAR Response Elements

This example describes the construction and functional analysis of several PPAR response elements which can be used in the hybrid promoters of the invention.

1-Production of a PPARs Response Unit of High Affinity

In order to obtain optimum induction by the PPAR ligands, several arrangements of PPRE multimers were designed and synthesized. The sequence of these regions is given below.

The element DR1 is the consensus site for binding of the heterodimer PPAR/RXR. The elements (DR1)2 17, (DR1)2 21 and (DR1)2 31 consist of two DR1s separated center to center by 17, 21 and 31 base pairs respectively.

```
DR1 (SEQ ID NO: 1)
CAAAACT AGGTCA A AGGTCA
(DR1)2 17 (SEQ ID NO:2)
CAAAACT AGGTCA A AGGTCA AAACT AGGTCA A AGGTCA
(DR1)2 21 (SEQ ID NO: 3)
CAAAACT AGGTCA A AGGTCA t CAAAACT AGGTCA A AGGTCA
(DR1)2 31 (SEQ ID NO: 4)
CAAAACT AGGTCA A AGGTCA tgtctttaggcc CAAAACT AGGTCA A AGGTCA
```

2-Binding Experiments 2-1 Binding of PPARγ

In order to verify the functional nature and the efficiency of the above PPRE regions, gel retardation experiments were carried out consisting in studying the binding between one of the four sequences above, radiolabeled beforehand, in the presence of increasing quantities (5 and 10 μl) of PPARγ and RXR proteins prepared in Cos-1 cells (PPARγ/RXR ratio=3:1). The results obtained are presented in FIG. 2.

These results show that the sequences constructed bind the heterodimer PPAR/RXR. The sequence DR1 binds a dimeric complex whereas the sequences (DR1)2 17, (DR1)2 21 and (DR1)2 31 bind the dimeric complex but also a retarded complex of high molecular weight which is thought to correspond to a double heterodimer PPAR/RXR. Moreover, the quantities of the dimeric and high-molecular weight complexes are variable from one sequence to another. This suggests that these three sequences bind the RXR/PPARγ complexes with a different cooperativity.

Figure 2:
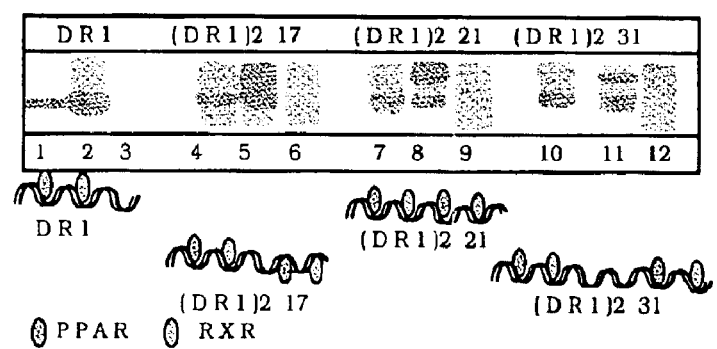
FIG. 2: Gel retardation binding analysis. The radiolabeled sequences DR1, (DR1)2 17, (DR1)2 21, (DR1)2 31 are incubated with 5 or 10 µl of Cos-1 extracts enriched with PPARγ and RXR. Lanes 1, 4, 7, 10 correspond to 5 µl and lanes 2, 5, 8, 11 to 10 µl of extracts. Lanes 3, 6, 9 and 12 correspond to 10 µl of nontransfected Cos-1 extracts.

To know if the complexes observed come from the production of PPARγ and from RXR in the Cos-1 cells, or alternatively from proteins present in these cells, these different sequences were incubated with extracts of non-transfected Cos-1 (10 μl). The intensity of the complexes formed with these extracts is very weak, which is in favor of the production of PPARγ and RXR proteins following the transfection of the cells (FIG. 2).

With the aim of studying the cooperativity of the binding of PPAR/RXR to these different sequences, gel retardation experiments placing increasing quantities of Cos-1 extracts enriched with PPAR and RXR (1 μl to 10 μl), followed by quantification of the radioactivity obtained, were carried out. The formation of the first PPAR/RXR dimer is characterized by the dissociation constant KdII, that of the double dimer, or tetramer, is characterized by the dissociation constant KdIV. The KdII/KdIV ratio (R) is the reflection of the cooperativity of the binding if it is greater than 1.

Figure 3:
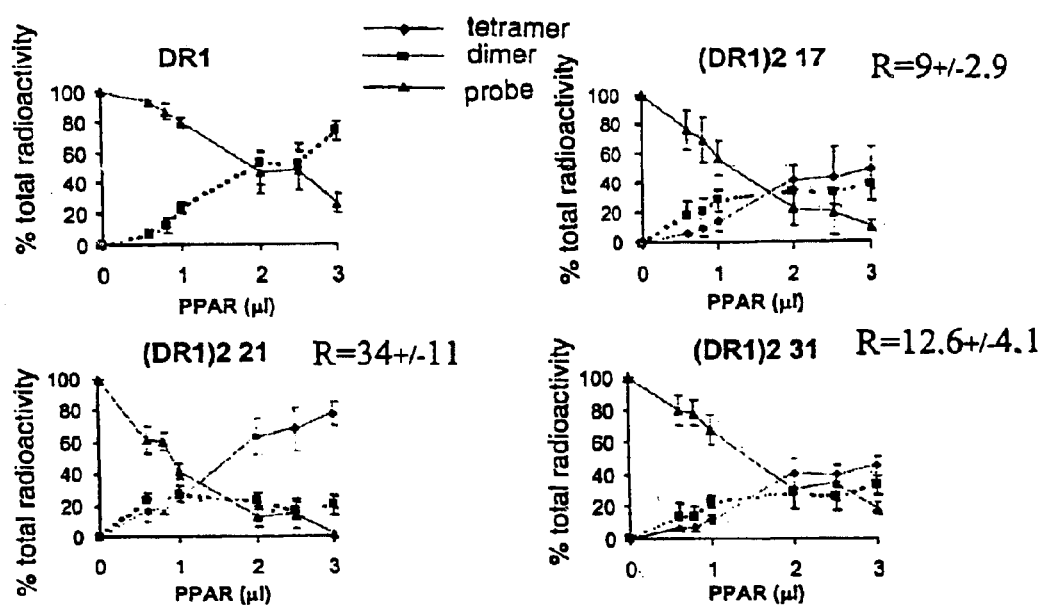
FIG. 3: Quantification of the radioactivity obtained in the dimeric and tetrameric bands and the free probe (PPARγ).

The various dimeric and tetrameric complexes and the free probe were quantified by means of a Phosphorimager and represented in FIG. 3. The cooperativity ratios were calculated by means of the abovementioned formula. The sequences (DR1)2 17 and (DR1)2 31 bind as many dimeric and tetrameric forms. The cooperativity ratios are 9 and 12.6 respectively. However, the sequence (DR1)2 21 exhibits a different binding profile. The dimeric form forms only 20% of the total binding, whereas the tetrameric form forms 80% of the total binding. The cooperativity ratio is 34 +/−11.

These results as a whole show that the three sequences used cooperatively bind PPAR and RXR. The sequence which exhibits the best cooperativity of binding is (DR1)2 21.

2-2 Binding of PPARα

Figure 4:
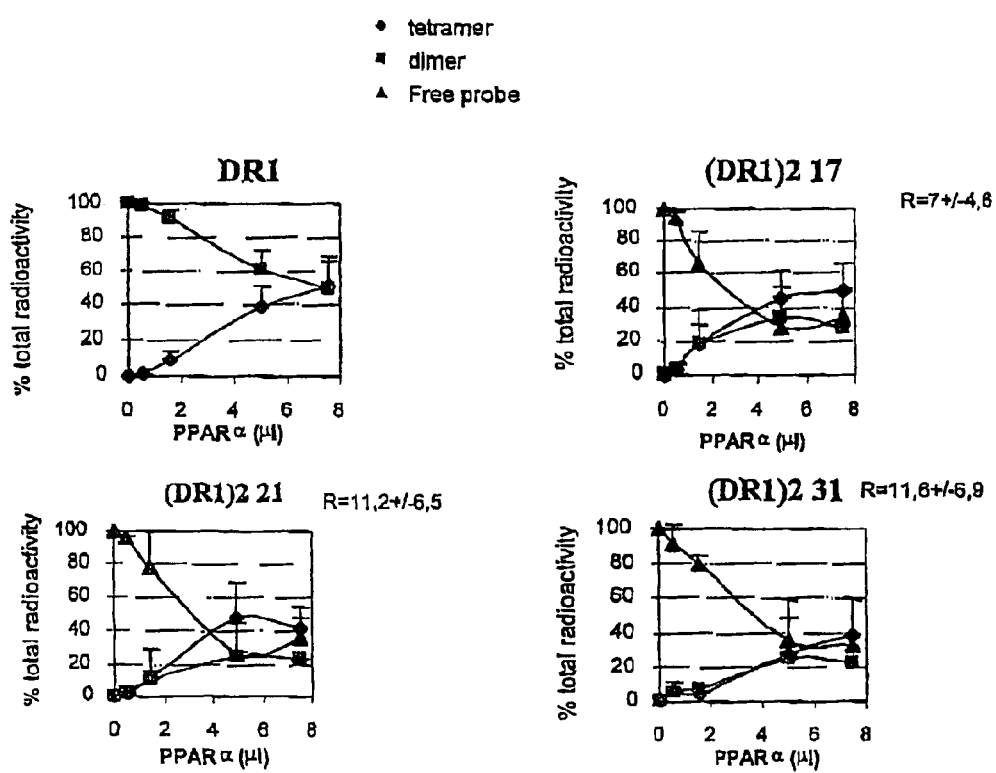
FIG. 4: Quantification of the radioactivity obtained in the dimeric and tetrameric bands and the free probe (PPARα).

Similar experiments were carried out with PPARα. The vector for expressing the α isoform of PPAR was transfected into Cos-1 cells. Total extracts of the latter were prepared as described in the section Materials and Methods. Gel retardation experiments using the four radiolabeled sequences and increasing quantities of Cos-1 extracts enriched with PPARα and RXR (rapport3/1) were carried out. The bands corresponding to the dimeric (D) or tetrameric (T) forms or the free probe (P) were cut out of the gel and then quantified by counting on a beta scintillation counter (FIG. 4). The thermodynamic model described above was applied with the aim of calculating the ratios of cooperativity of binding of the PPARα/RXR heterodimer to the different sequences studied.

By contrast to what was observed with PPARγ, the cooperativity ratios obtained with the sequences (DR1)2 21 and (DR1)2 31 are equivalent (R=11.2 and 11.6 respectively). The cooperativity ratio obtained in the case of the element (DR1)2 17 is less than the preceding two (R=7). In this case also, the three synthesized sequences cooperatively bind PPARα, the sequences (DR)2 21 and (DR1) 2 31 exhibiting the best binding cooperativity.

Example 2

Construction and Functional Analysis of a Vector Comprising a Hybrid Promoter

This example describes construction of plasmids comprising a hybrid promoter of the invention, and demonstrates its induction properties by various inflammation mediators.

1) Construction of the Plasmids and Functional Tests

The fragment −247/+20 of the promoter of sPLA2 IIA (SEQ ID NO:5) was subcloned upstream of the CAT reporter vector for the plasmid PUC-SH-CAT. Upstream of this promoter, the different PPRE sequences cited above (SEQ ID NO: 1–4) were inserted.

Figure 5:
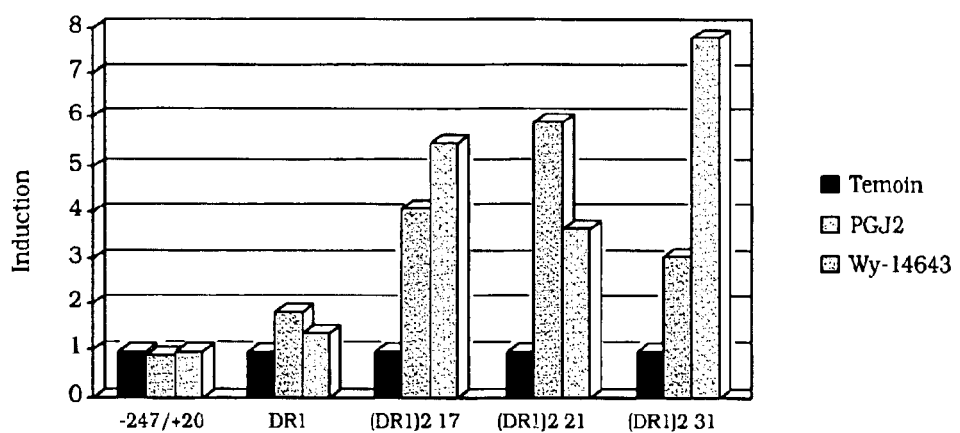
FIG. 5: Effect of PGJ2 (PPARγ inducer) and Wy-14643 (PPARα inducer) on the synthetic promoters.

The rabbit chondrocytes were then transfected with the CAT constructs containing the different arrangements of PPRE (DR1) placed upstream of the minimal promoter of sPLA2-IIA. 15 deoxy $\Delta^{12-14}$ PGJ2 (10 μM) (activator of PPARγ) or Wy-14643 (200 μM) (activator of PPARα) were then added to the culture medium for 24 hours. The results obtained are presented in FIG. 5.

The results show that the minimal promoter (−247/+20) of sPLA2-IIA, which does not contain known PPRE sites, is not activated by PGJ2 or by Wy 14643. However, the different arrangements of DR1 are activated at different levels by the inducers of PPARγ or of PPARα. It is possible to classify them in the following increasing order: DR1< $(DR1)_{2\ 17}$=$(DR1)_{2\ 31}$<$(DR1)_{2\ 21}$ in the case of PPARγ. On comparing the binding results with the functional results, it is observed that the sequence (DR1) 2 21, which has the best binding cooperativity, exhibits the best functional syngergy.

In the case of PPARα, the order of inducibility by Wy-14643 is different from that established in the case of PGJ2. DR1<$(DR1)_{2\ 21}$<$(DR1)_{2\ 17}$<$(DR1)_{2\ 31}$. The gel retardation experiments are not in perfect agreement with the transient transfection experiments. The binding experiments showed that the sequences $(DR1)_{2\ 21}$ and $(DR1)_{2\ 31}$ bind PPARα with the same cooperativity (R=11) whereas the sequence $(DR1)_{2\ 17}$ exhibits a lower binding cooperativity (R=7).

2-Combined Effects of IL-1, of Glucocorticoids and of Inducers of PPARa (Fibrates) and PPARγ (15 dioxy Δ12–14 PGJ2) on the Synthetic Promoter:

Rabbit chondrocytes were then transfected, either with the minimal promoter of sPLA2-IIA, or with the sequence $(DR1)_{2\ 21}$ placed upstream of the latter (hybrid promoter). PGJ2 (10 μM) and/or IL-1 (10 ng/ml) are added to the culture medium.

Figure 6:
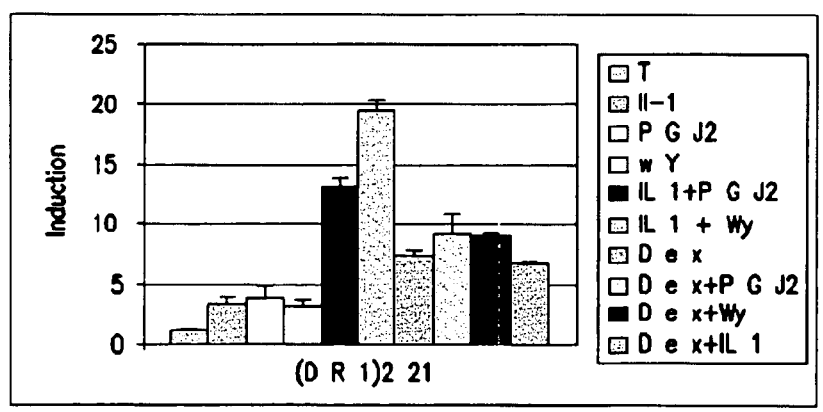
FIG. 6: The rabbit chondrocytes were transfected with the plasmid containing the element (DR1)2 21-(−247/+20) sPLA2-CAT. The different inducers mentioned above are added to the culture medium.
Figure 7B:
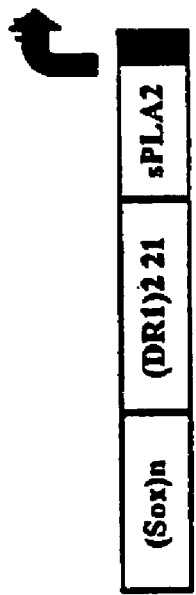
FIGS. 7A and 7B: Schematic representation of the constructs into which elements of the type II collagen promoter capable of binding the SOX factors have been integrated respectively downstream and upstream of the hybrid construct (DR1)2 21-promoter of sPLA2 IIA.
Figure 7A:
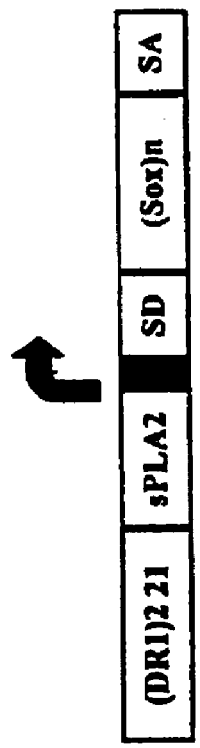

The results obtained are presented in FIG. 6. These results show that IL-1 induces the promoter of sPLA2-IIA 6 fold. The prostaglandin J2 or Wy-14643 have no effect on this promoter (results not shown). In the case of the construct (DR2 21-(−247/+20) sPLA2-CAT, IL-1 and PGJ2 induce this promoter 4 fold. The two combined products have a synergistic effect (13-fold induction relative to the basal activity) (FIG. 6).

This same type of experiment was carried out with Wy-14643. This compound is an inducer specific for PPARα. Wy-14643 (200 μM) activates the transcription of the construct (DR)2 21-(−247/+20) sPLA2-CAT about 3 to 4 fold. The effect of the combined IL-1 and Wy-14643 is synergistic (20-fold induction).

The effect of dexamethasone was moreover tested on the synthetic promoter (−247/+20)-(DR1)2 21-CAT, either alone or combined with Wy-16463, PGJ2, or IL-1. Dexamethasone activates the transcription of this promoter by about 6 fold. These results show that the circulating glucocorticoids such as cortisol, or administered during a treatment, can activate this hybrid promoter.

The effect of some nonsteroidal anti-inflammatory drugs such as indomethacin or ibuprofen was also tested on the synthetic promoters. The results obtained show that indomethacin ($10^{-4}$ M) activates by about fivefold the construct (DR1)2 21-(−247/+20)-CAT whereas ibuprofen ($10^{-4}$ M) activates this promoter 17 fold.

Finally, the levels of transcriptional activities reached by a viral promoter, such as the RSV (Rous Sarcoma Virus) promoter, and that of the synthetic promoter were compared. The basal transcriptional activity of the synthetic promoter is low, it is less than 5% of the activity of the RSV viral promoter. After induction with the different effectors, the synthetic promoter exhibits a level of transcriptional activity which reaches 40% of that of RSV (results not shown). The promoter constructed according to the present invention is therefore characterized by a high induced transcriptional activity comparable to the viral vectors currently used in gene therapy, and a low basal activity.

Conclusions

Hybrid synthetic promoters inducible by the components of inflammation, that is to say the pro-inflammatory cytokines such as IL-1β, as well as the pro-inflammatory fatty acids, such as the prostaglandins or the leukotrienes were developed. Furthermore, the circulating or locally administered glucocorticoids as well as the nonsteroidal anti-inflammatory drugs, such as ibuprofen or indomethacin, are capable of activating the transcription of these promoters. These promoters therefore constitute an effective means of modulating the activity of genes according to whether an anti-inflammatory treatment is administered or not. These characteristics make it possible to envisage a controllable (on/off) effect on the synthesis of the medicament gene. It is important to note that this synthetic promoter has a very low basal activity, whereas it has a transcriptional activity induced by the endogenous or exogenous stimuli comparable to the viral vectors in efficiency.

Bibliographic References

Amin A R, Attur M, Patel R N, Thakker G D, Marshall P J, Rediske J, Stuchin S A, Patel I R, Abramson S B (1997) *Superinduction of cyclooxygenase-2 activity in human osteoarthritis-affected cartilage. Influence of nitric oxide.* J Clin Invest 99 (6): 1231–1237.

Berenbaum F, Thomas G, Poiraudeau S, Bereziat G, Corvol M T, Masliah J (1994) *Insulin-like growth factors counteract the effect of interleukin 1 beta on type II phospholipase $A_2$ expression and arachidonic acid release by rabbit articular chondrocytes.* FEBS Lett 340 (1–2): 51–55.

Bingham C. O. $3^{rd}$ Murakami M., Fujishima H., Hunt J. E., Austen K. F., Arm J. P. (1996) *A heparin-sensitive phospholipase $A_2$ and prosaglandin endoperoxide synthase-2 are functionally linked in the delayed phase of prostaglandin D2 generation in mouse bone marrow-derived mast cellls.* J Biol. Chem. 271: 25936–25944.

Camper L, Heinegard D, Lundgren-Akerlund E (1997) *Integrin alpha2beta1 is a receptor for the cartilage matrix protein chondroadherin.* J Cell Biol; 138(5):1159–6

Chevalier, X *Physiopathologie de l'arthrose* [*Physiopathology of osteoarthritis*]. (1998) *La Presse Médicale.* 27(2). 75–92.

Clark J D, Lin L L, Kriz R W, Ramesha C S, Sultzman L A, Lin A Y, Milona N, Knopf J (1991) *A novel arachidonic acid-selective cytosolic $PLA_2$ contains a $Ca^{2+}$ dependent translocation domain with homology to PKC and GAP.* Cell 65: 1043–1051.

Dean, J, Martel-Pelletier, J, Pelletier, J P, et al. *Evidence for metalloprotease and metalloprotease inhibitors imbalance in human osteoarthritic cartillage. Arthritis Rheum.* 1990, 33, 1466–76

Desbois C, Massé T, Madjar J J. (1992) *Optimization of the CAT assay procedure by determining the initial rate of the enzymatic reaction. Trends Genet*; 8: 300–30

Devchand, R P, Keller, H, Peters, J M, Vazquez, M, Gonzalez, F J, Wahli, W. *The PPAR?-leukotriene B4 pathway to inflammation control.* (1996) Nature, 384, 39–43.

Di Battista J A, Dore S, Martel-Pelletier J P (1996) *Prostaglandin E2 stimulates incorporation of proline into collagenase digestible proteins in human articular chondrocytes: identification of an effector autocrine loop involving insulin-like growth factor I. Mol Cell Endocrinol* 123: 27–35.

Geng Y, Blanco F J, Cornelisson M, Lotz M (1995) *Regulation of cyclooxygenase-2 expression in normal human articular chondrocytes.* J Immunol 155 (2): 796–801

Guingamp C, Gegout-Pottie, Philippe L, Terlain B, Netter P, Gillet P. (1997) *Mono-iodoacetate-induced experimental osteoarthriris. Arthritis Rhumatism.* 40:1670–1679.

Hornebeck W, Lafuma, C. *Les métalloprotéinases matricielles* [*Matrix metalloproteinases*]. (990) *CR Soc biol.* 185, 1466–76

Hulkower K I, Hope W C, Chen T, Anderson C M, Coffey J W, Morgan D M (1992) *Interleukin-1? stimulates cytosolic phospholipase $A_2$ in rheumatoid synovial fibroblasts. Biochem. Biophys. Res. Commun.* 184: 712–718.

Jacques, C., Bereziat, G., Humbert, L., Olivier, J. L., Corvol, M. T., Masliah, J., and Berenbaum, F. (1997). *Posttranscriptional effect of insulin-like growth factor-I on interleukin-1 beta-induced type II-secreted phospholipase A2 gene expression in rabbit articular chondrocytes.* J Clin Invest 99, 1864–72.

Jpenberg A I, Jeannin E, Wahli W, Desvergne B. (1997) *Polarity and specific sequence requirements of peroxisome proliferator-activated receptor (PPAR)/retinoid X receptor heterodimer binding to DNA.*

Kim Y, Fischer S M (1998)*Transcriptional regulation of cyclooxygenase-2 in mouse skin carcinoma cells. Regulatory role of CCAAT/enhancer-binding proteins in the differential expression of cyclooxygenase-2 in normal and neoplastic tissues.* J Biol Chem 16; 273(42):27686–9

Klapisz E, Ziari M, Wendum L, Koumanov K, Brachet C,-Ducos, Olivier J L, Béréziat G, Trugnan G, Masliah J (1999) *N- and C-terminal plasma membrane anchoring modulate differently agonist-induced activation of cytosolic phospholipase A2 (publication en cours).*

Kliewer, S A, Lenhard, J M, Wilson, T M, Patel, I, Morris, D C, Lehmann, J M. *A prostaglandine J2 metabolite binds peroxisome proliferator-activated receptor ? and promotes adipocyte differentiation.* (1995) Cell. 83, 813–819

Knott I, Dieu M, Burton M, Houbion A, Remacle J, Raes M (1994) *Induction of cyclooxygenase by interleukin 1:* comparative study between human synovial cells and chondrocytes. *J Rheumatol* 21 (3): 462–466.

Kreiss P, Scherman D (1999) *Optimisation des plasmides et des vecteurs synthétiques pour la thérapie génique* [Optimization of the synthetic vectors and plasmids for gene therapy]. *Médecine/Sciences*, 15: 669–676

Krey, G, Braissant, O, L'Horset, F, Kalkhoven, E, Perroud, M, Parker, M G, Wahli, W. *Fatty acids, eicosanoids, and hypolipidemic agents identified as ligands of peroxisome proliferator-activated receptors by coactivator-dependent receptor ligand assay.* (1997) *Mol. Endocrinol.* 11, 779–791.

Kuwata H., Nakatani Y., Murakami M. & Kudo I. (1998) *Cytosolic phospholipase $A_2$ is required for cytokine-induced expression of type IIA secretory phospholipase $A_2$ that mediates optimal cyclooxygenase-2-dependent delayed prostaglandin E2 generation in rat 3Y1 fibroblasts.* *J. Biol. Chem.* 273: 1733–40.

Leevers S J, Paterson H F, Marshall C J (1994) *Requirement for Ras in Raf activation is overcome by targeting Raf to the plasma membrane.* *Nature* 369, 411–414.

Lefebvre, V & de Crombrugghe, B. *Toward understanding SOX9 function in chondrocyte differentiation.* *Matrix Biol.* 16, 529–540

Lefebvre, V, Huang, W, Harley, V R, Goodfellow, P N & de Crombrugghe, B. *SOX9 is a potent activator of the chondrocyte-specific enhancer of the pro alpha1(II) collagen gene.* (1997) *Mol. Cell. Biol.* 17, 2336–2346

Lehmann J M, Lenhard J M, Oliver B B, Gordan M R, Kliewer S A. (1997). *Peroxisome Proliferator-activated receptord a and are ectivated by indomethacin and other non-steroidal anti-inflammatory drugs.* *J. Biol. Chem.* 272:3406–3410.

Lin M. K., Farewell V., Vadas P., Bookman A. A., Keystone E. C., Pruzanski W. (1996) *Secretory phospholipase A2 as an index of disease in rheumatoid arthritis. Prospective double blind study of 212 patients.* *J. Rheumatol.* 23: 112–1166.

Makihira S, Yan W, Ohno S, Kawamoto T, Fujimoto K, Okimura A, Yoshida E, Noshiro M, Hamada T, Kato Y. *Enhancement of cell adhesion and spreading by a cartilage-specific noncollagenous protein, cartilage matrix protein (CMP/Matrilin-1), via integrin alpha1 beta1.* (999) *J Biol Chem*, 274(16):11417–2

Mukhopadhyay, K, Lefebvre V, Zhou, G, Garofalo, S, Kimura, J H and de Crombrugghe, B. *Use of a new rat chondrosarcoma cell line to delineate a 119-base pair chondrocyte-specific enhancer element and to define active promoter segments in the mouse pro-alpha1 (II) collagen gene* (1995) *J. Biol. Chem.* 270, 27711–19.

Nevalainen T J, Marki F, Kortesuo P T, Grutter M G, Di Marco S, Schmitz A (1993) *Synovial type (group II) phospholipase $A_2$ in cartilage.* *J Rheumatol* 20 (2): 325–330.

Pruzanski W., Albin-Cook K, Laxer R. M., MacMillan J, Stefanski E., Vadas P., and Silverman E. D. (1994) *Phospholipase $A_2$ in juvenile rheumatoid arthritis: Correlation to disease type and activity.* *J. Rheumatol.* 21: 1951–1954.

Schoonjans, K, Staels, B, Auwrex, J. *The peroxisome proliferator activated receptors (PPARs) and their effects on lipid metabolism and adipocyte differentiation.* (1996) *Biochem. Biophys. Acta.* 1302, 93–109.

Seilhamer J J, Pruzanski W, Vadas P., Plant S, Miller J A, Kloss J, Johnson L K (1989) *Cloning and recombinant expression of phospholipase $A_2$ present in rheumatoid arthritic synovial fluid.* *J. Biol. Chem.* 264: 5335–5338.

Stokoe D, Macdonald S G, Cadwallader K, Symons M, Hancock J F (1994) *Activation of Raf as a result of recruitment to the plasma membrane.* *Science* 264, 1463–1467.

Thomas B, Humbert L, Crofford L, Biu X, Berenbaum F, Olivier J L. *Critical role of C/EBPd and C/EBPb factors in the stimulation of cyclooxygenase-2 gene transcription by interleukine-1b in primary culture chondrocyte* (publication pending).

Zhou, G, Garofalo, S, Mukhopadhyay, K, Lefebvre, V, Smith, CN, Eberspaecher, H and de Crombrugge, B. *A 182 bp fragment of the mouse alpha 1 (II) collagen gene is sufficient to direct chondrocyte expression in transgenic mice* (1995) *J. Cell. Sci.* 108, 3677–84.

Zlatkine P, Mehul B, Magee A I (1997) *Retargeting of cytosolic proteins to the plasma membrane by the Lck protein tyrosine kinase dual acylation motif.* *J Cell. Science* 110, 673–679.

---

What is claimed is:

1. A hybrid promoter comprising:
   a) a peroxisome proliferator activated receptor response element (PPAR response element) comprising at least one PPAR-binding site; and
   b) a promoter of a IIA-1 nonpancreatic secreted phospholipase A2 (PLA2s) gene comprising SEQ ID NO:5 or comprising a sequence a PLA2s gene comprising at least residues 51 to 61, 23 to 32, 148 to 155, 5 to 170 or 51 to 170 of SEQ ID NO:5.

2. The hybrid promoter according to claim 1, wherein the PPAR response element has repetition of the same PPAR-binding site or a combination of different PPAR-binding sites.

3. The hybrid promoter according to claim 2, wherein the PPAR response element comprises one or more sites having the nucleic acid sequence of SEQ ID NO:1.

4. The hybrid promoter according to claim 1, wherein the PPAR response element comprises the nucleic acid sequence of one of SEQ ID NOS:1, 2, 3 or 4.

5. The hybrid promoter according to claim 1, wherein said promoter of a PLA2s gene is induced by interleukin-1B.

6. The hybrid promoter according to claim 1, wherein said PPAR response element is positioned 5' upstream of said sequence of said PLA2s gene comprising at least residues 51 to 61, 23 to 32, 148 to 155, 5 to 170 or 51 to 170 of SEQ ID NO:5.

7. The hybrid promoter according to claim 1, comprising an additional nucleic acid sequence that confers tissue specificity.

8. The hybrid promoter according to claim 7, wherein said additional nucleic acid sequence confers specificity for chondrocytic cells.

9. The hybrid promoter according to claim 7, wherein said additional nucleic acid sequence comprises SEQ ID NO:7.

10. An isolated nucleic acid comprising a nucleic acid sequence selected from the group consisting of SEQ ID NOS:2, 3, 4 and 5.

11. The isolated nucleic acid according to claim 10, further comprising a nucleic acid sequence encoding an anti-inflammatory polypeptide.

12. A vector comprising a nucleic acid sequence comprising said hybrid promoter according to claim 1.

13. A vector comprising a nucleic acid sequence comprising said hybrid promoter according to claim 6.

14. The vector according to claim 12, wherein said vector is a plasmid.

15. The vector according to claim 13, wherein said vector is a plasmid.

16. A composition comprising (i) the isolated nucleic acid according to claim 10 and (ii) a PPAR activator.

17. A composition comprising (i) the vector according to claim 12 and (ii) a PPAR activator.

18. A composition comprising (i) the vector according to claim 13 and (ii) a PPAR activator.

19. A nucleic acid comprising a sequence selected from the group consisting of SEQ ID NO:2, SEQ ID NO:3 and SEQ ID NO:4.

20. A nucleic acid comprising the sequence of SEQ ID NO:6.

21. An isolated cell comprising the hybrid promoter according to claim 1.

22. An isolated cell comprising the hybrid promoter according to claim 12.

23. An isolated cell comprising the hybrid promoter according to claim 13.

24. A hybrid promoter comprising:
   a) a peroxisome proliferator activated receptor response element (PPAR response element) selected from the group consisting of SEQ ID NO:1, SEQ ID NO:2, SEQ ID NO:3 and SEQ ID NO:4 linked to
   b) a promoter of a IIA-1 nonpancreatic secreted phospholipase (PLA2s) gene comprising SEQ ID NO:5 or comprising a sequence of said PLA2s gene comprising at least residues 51 to 61, 23 to 32, 148 to 155, 5 to 170 or 51 to 170 of SEQ ID NO:5.

25. The hybrid promoter according to claim 24, wherein said peroxisome proliferator activated receptor response element (PPAR response element) is directly linked to said promoter of a IIA-1 nonpancreatic secreted phospholipase A2 (PLA2s) gene comprising SEQ ID NO:5 or said sequence of said PLA2s gene comprising at least residues 51 to 61, 23 to 32, 148 to 155, 5 to 170 or 51 to 170 of SEQ ID NO:5.

* * * * *

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: PPRE element

<400> SEQUENCE: 1
caaaactagg tcaaaggtca                    20

<210> SEQ ID NO 2
<211> LENGTH: 38
<212> TYPE: DNA
<213> ORGANISM: Artificial Sequence
<220> FEATURE:
<223> OTHER INFORMATION: PPRE element

<400> SEQUENCE: 2

-continued caaaactagg tcaaaggtca aaactaggtc aaaggtca                    38

<210> SEQ ID NO 3
<211> LENGTH: 41
<212> TYPE: DNA
<213> ORGANISM: Artificial Sequence
<220> FEATURE:
<223> OTHER INFORMATION: PPRE element

<400> SEQUENCE: 3
caaaactagg tcaaaggtca tcaaaactag gtcaaaggtc a                41

<210> SEQ ID NO 4
<211> LENGTH: 52
<212> TYPE: DNA
<213> ORGANISM: Artificial Sequence
<220> FEATURE:
<223> OTHER INFORMATION: PPRE element

<400> SEQUENCE: 4
caaaactagg tcaaaggtca tgtctttagg cccaaaacta ggtcaaaggt ca    52

<210> SEQ ID NO 5
<211> LENGTH: 271
<212> TYPE: DNA
<213> ORGANISM: Artificial Sequence
<220> FEATURE:
<223> OTHER INFORMATION: Fragment of the PLA2s promoter

<400> SEQUENCE: 5
cgcggcaaaa ctgcctgaaa tgtgttttgg catcagctac tgacacgtaa ggtttcccaa    60
tcctcaactc tgtcctgcca gctgatgagg ggaaggaaag ggattaccta ggggtatggg   120
cgaccaatcc tgagtccacc aactgaccac gcccatcccc agccttgtgc ctcacctacc   180
cccaacctcc cagagggagc agctatttaa ggggagcagg agtgcagaac aaacaagacg   240
gcctggggat acaactctgg agtcctctga g                                 271

<210> SEQ ID NO 6
<211> LENGTH: 332
<212> TYPE: DNA
<213> ORGANISM: Artificial Sequence
<220> FEATURE:
<223> OTHER INFORMATION: PPRE/PLA2s hybrid promoter

<400> SEQUENCE: 6
gtaccaattc gacaaaacta ggtcaaaggt catcaaaact aggtcaaagg tcaaattcga    60
acgcggcaaa actgcctgaa atgtgttttg gcatcagcta ctgacacgta aggtttccca   120
atcctcaact ctgtcctgcc agctgatgag gggaaggaaa gggattacct aggggtatgg   180
gcgaccaatc tgagtccac caactgacca cgcccatccc cagccttgtg cctcacctac   240
ccccaacctc ccagagggag cagctattta aggggagcag gagtgcagaa caaacaagac   300
ggcctgggga tacaactctg gagtcctctg ag                                332

<210> SEQ ID NO 7
<211> LENGTH: 944
<212> TYPE: DNA
<213> ORGANISM: Artificial Sequence
<220> FEATURE:
<223> OTHER INFORMATION: Sequence conferring specificity of expression

<400> SEQUENCE: 7

```
tgccggcctc gcggtgagcc ctgatccgcc tcggggctcc ccagtcgctg gtgctgctga      60
cgctgctcat cgccgcggtc ctacggtgtc agggccagga tgcccgtaag tcgcccgccg     120
cccctgccta cttccctgac ttgtgaccct tttcctccta ctccctcccc caagtactag     180 gatccccta gagcttgcag atctgggatt ggcagcgatg gcttccagat gggctgaaac      240
cctgcccgta tttatttaaa ctggttcctc gtggagagct gtgaatcggg ctctgtatgc     300
gcttgagaaa agccccattc atgagaggca aggcccagtg ggtcccccaa ctccccgacc     360
cccctctccc acaatgcaca gcctccccgc cctcatcccc cccccacccc ccgtgcccgc     420
ctgccgccac cttcagatcg atctgggatt ggcagcgatg gcttccagat gggctgaaac     480
cctgcccgta tttatttaaa ctggttcctc gtggagagct gtgaatcggg ctctgtatgc     540
gcttgagaaa agccccattc atgagaggca aggcccagtg ggtcccccaa ctccccgacc     600
cccctctccc acaatgcaca gcctccccgc cctcatcccc cccccacccc ccgtgcccg      660 cctgccgcca cctccagatc tccagctaga ggatctgcga ctctagggtt cgaaatcgat    720
aagccaagct ctagtggatc ccccgggctg cagatctgta gggcgcagta gtccagggtt    780
tccttgatga tgtcatactt atcctgtccc ttttttttcc acagctcgcg gttgaggaca    840
aactcttcgc ggtctttcca gtggggatcg acggtatcga taagcttgat gatctgtgac    900
atggcggatc ccgtcgtttt acaacgtcgt gactgggaaa accc                     944
```